(12) United States Patent
Ouchi et al.

(10) Patent No.: US 8,912,366 B2
(45) Date of Patent: Dec. 16, 2014

(54) PROCESS FOR PREPARING ADAMANTANE POLYOL

(75) Inventors: Takashi Ouchi, Yokkaichi (JP); Yoshio Nishimura, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 102 days.

(21) Appl. No.: 13/988,559

(22) PCT Filed: Nov. 15, 2011

(86) PCT No.: PCT/JP2011/076228
§ 371 (c)(1),
(2), (4) Date: May 21, 2013

(87) PCT Pub. No.: WO2012/070423
PCT Pub. Date: May 31, 2012

(65) Prior Publication Data
US 2013/0245329 A1    Sep. 19, 2013

(30) Foreign Application Priority Data

Nov. 22, 2010 (JP) ................................. 2010-259910

(51) Int. Cl.
| | |
|---|---|
| *C07C 29/48* | (2006.01) |
| *C07C 35/44* | (2006.01) |
| *B01J 23/96* | (2006.01) |
| *B01J 20/34* | (2006.01) |
| *B01J 20/16* | (2006.01) |
| *B01J 20/00* | (2006.01) |
| *B01J 20/02* | (2006.01) |
| *B01J 20/04* | (2006.01) |

(52) U.S. Cl.
CPC .............. *C07C 29/48* (2013.01); *B01J 23/96* (2013.01); *B01J 20/34* (2013.01); *B01J 20/0225* (2013.01); *B01J 20/048* (2013.01); *B01J 20/16* (2013.01); *C07C 2103/74* (2013.01)
USPC ........................................... 568/818; 502/25

(58) Field of Classification Search
USPC ........................................... 568/818; 502/25
See application file for complete search history.

(56) References Cited

U.S. PATENT DOCUMENTS

| | | | | |
|---|---|---|---|---|
| 4,686,198 | A * | 8/1987 | Bush et al. ..................... | 502/25 |
| 6,187,967 | B1 | 2/2001 | Kakuda et al. | |
| 6,333,438 | B1 | 12/2001 | Kakuda et al. | |
| 6,342,462 | B1 * | 1/2002 | Kulprathipanja ............... | 502/25 |
| 6,570,042 | B2 | 5/2003 | Kakuda et al. | |
| 7,169,954 | B2 | 1/2007 | Mizuno et al. | |
| 2002/0040170 | A1 | 4/2002 | Kakuda et al. | |
| 2004/0204597 | A1 | 10/2004 | Mizuno et al. | |
| 2006/0094899 | A1 | 5/2006 | Mizuno et al. | |

FOREIGN PATENT DOCUMENTS

| | | |
|---|---|---|
| JP | 2000-178301 A | 6/2000 |
| JP | 2000-219646 A | 8/2000 |
| JP | 2001-031603 A | 2/2001 |
| JP | 2001-335519 A | 12/2001 |
| JP | 2002-167342 A | 6/2002 |
| JP | 2003-201526 A | 7/2003 |
| JP | 2004-000894 A | 1/2004 |
| JP | 2004-339105 A | 12/2004 |
| JP | 2005-075675 A | 3/2005 |
| JP | 2009-057611 A | 3/2009 |
| WO | 2005/097717 A1 | 10/2005 |

OTHER PUBLICATIONS

International Search Report dated Feb. 21, 2012, issued in International Application PCT/JP2011/076228.
International Preliminary Patentability Report dated Feb. 21, 2012, issued in International Application PCT/JP2011/076228.

* cited by examiner

*Primary Examiner* — Jafar Parsa
*Assistant Examiner* — Medhanit Bahta
(74) *Attorney, Agent, or Firm* — Fitch, Even, Tabin & Flannery LLP

(57) ABSTRACT

The present invention provides a process for preparing an adamantane polyol by reacting an adamantane with a ruthenium compound and a hypochlorite in a biphasic water/organic solvent system. The process includes the steps of adding an inorganic adsorbent to a reaction system; and adding an alkali to a reaction mixture to separate the ruthenium compound together with the inorganic adsorbent, and reusing the separated ruthenium compound and inorganic adsorbent in a subsequent reaction.

9 Claims, No Drawings

PROCESS FOR PREPARING ADAMANTANE POLYOL

CROSS-REFERENCE TO RELATED APPLICATIONS

This Application is a U.S. National Stage Application filed under 35 U.S.C. §371 of International Application PCT/JP2011/076228, filed Nov. 15, 2011, designating the United States, which claims priority from Japanese Patent Application 2010-259910, filed Nov. 22, 2010, the complete disclosures of which are hereby incorporated herein by reference in their entirety for all purposes.

TECHNICAL FIELD

The present invention relates to a process for preparing an adamantane polyol which is useful as an intermediate material for a highly functional polymer, a synthetic lubricant, a plasticizer or the like, or as an intermediate for an organic chemical such as, for example, a pharmaceutical or agricultural drug.

BACKGROUND ART

According to a process for preparing an adamantane polyol (adamantane diol, adamantane triol, etc.), an adamantane is reacted with a ruthenium compound and a hypochlorite in a biphasic water/organic solvent system (see Patent Documents 1 through 3). However, a ruthenium compound is costly and thus needs to be recovered and reused. Ruthenium may have various valences and is difficult to be recovered as a single compound. This causes a problem that the recovery ratio is low.

In order to solve this problem, there are the following processes: a process by which an oxidant is added to a post-reaction solution to put ruthenium into a highly oxidized state, and ruthenium in such a state is transferred to an organic phase and recovered (see Patent Document 4); a process by which a ruthenium-containing material is mixed with an alkali hydroxide, then the mixture is reacted with an oxidant to extract ruthenium, and the extracted ruthenium is reduced by a lower alcohol and recovered (see Patent Document 5); and a process by which a ruthenium-containing material is dissolved in an alkali, an oxidant is added thereto to exude ruthenium, and the resultant ruthenium is reduced in a wet manner, washed with an acid and then recovered (see Patent Document 6).

However, these processes all require complicated steps in order to allow a ruthenium compound to be reused as a catalyst for an oxidation reaction, and also have a problem in terms of cost because a reductant or the like is needed.

CITATION LIST

Patent Literature

Patent Document 1: Japanese Laid-Open Patent Publication No. 2000-219646
Patent Document 2: Japanese Laid-Open Patent Publication No. 2001-335519
Patent Document 3: Japanese Laid-Open Patent Publication No. 2004-339105
Patent Document 4: Japanese Laid-Open Patent Publication No. 2001-031603
Patent Document 5: Japanese Laid-Open Patent Publication No. 2003-201526
Patent Document 6: Japanese Laid-Open Patent Publication No. 2009-057611

SUMMARY OF INVENTION

Technical Problem

The present invention has an object of providing a process for preparing an adamantane polyol, which is capable of separating and recovering a ruthenium compound used as a catalyst at high yield and easily so that the ruthenium compound can be provided to a subsequent reaction.

Solution to Problem

As a result of active studies, the present inventors found that in a process of reacting an adamantane with a ruthenium compound and a hypochlorite in a biphasic water/organic solvent system, by adding an inorganic adsorbent to the reaction system, the ruthenium compound can be recovered easily and provided to be reused in an oxidation reaction, and thus completed the present invention.

Namely, the present invention is directed to a process for preparing an adamantane polyol by reacting an adamantane represented by general formula (1) with a ruthenium compound and a hypochlorite in a biphasic water/organic solvent system, the process comprising the steps of adding an inorganic adsorbent to a reaction system; and adding an alkali to a reaction mixture to separate the ruthenium compound together with the inorganic adsorbent, and reusing the separated ruthenium compound and ruthenium compound in a subsequent reaction.

[Chemical formula 1]

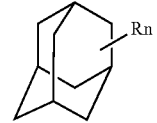

(1)

(in the formula, a substituent Rn independently represents an alkyl group, an aryl group, a cycloalkyl group, a hydroxyl group, an alkoxy group, an aryloxy group, an acyloxy group, or a halogen group; and n is an integer of 0 to 13).

Advantageous Effects of Invention

According to the present invention, a ruthenium compound, which is usable as a catalyst for an oxidation reaction and is costly, can be recovered at high yield in a simple manner, and reactivation thereof can be made easily.

DESCRIPTION OF EMBODIMENTS

According to the present invention, an adamantane represented by general formula (1) shown above is used. In general formula (1), a substituent Rn independently represents an alkyl group having a carbon number of 1 to 10 such as a methyl group, an ethyl group, a propyl group, a butyl group, a hexyl group or the like; an aryl group such as a phenyl group, a naphtyl group or the like; a cycloalkyl group such as a cyclohexyl group, a cyclooctyl group or the like; a hydroxyl group; an alkoxy group having a carbon number of 1 to 10 such as a methoxy group, an ethoxy group, a propoxy group, a butoxy group, a hexyloxy group or the like; an aryloxy group such as a phenoxy group or the like; an acyloxy group having a carbon number of 2 to 6 such as an acetyloxy group, a propionyloxy group, a butylyloxy group or the like; or a halogen group such as a fluoro group, a chloro group, a bromo group, an iodine group or the like. Among these groups, the substituent Rn is preferably an alkyl group having a carbon number of 1 to 6, and is more preferably an alkyl group having a carbon number of 1 to 4.

A ruthenium compound used in the present invention may be ruthenium metal, ruthenium dioxide, ruthenium tetraoxide, ruthenium hydroxide, ruthenium chloride, ruthenium bromide, ruthenium iodide, ruthenium sulfate or a hydrate thereof. These may be used independently or in a mixed state. From the viewpoint of suppressing the amount of ruthenium, which is costly, the ruthenium compound is preferably used in an amount of 0.005 to 2.0 mol per 1 mol of the adamantane used as the material. A content of 0.01 to 0.4 mol per 1 mol of the adamantane is more preferable from the viewpoint of suppressing a side reaction.

As a hypochlorite used in the present invention, sodium hypochlorite is preferable. The hypochlorite is used in the form of an aqueous solution containing the hypochlorite at a concentration of 6 to 35% by weight. When the concentration of the hypochlorite is lower than this range, the amount of the aqueous phase is too large. As a result, the efficiency of extracting the reaction product from the aqueous phase is decreased, and also a load is imposed on a liquid waste treatment. By contrast, when the concentration of the hypochlorite is higher than this range, a side reaction is likely to occur and thus the yield of the adamantane polyol is decreased. In order to obtain an adamantane polyol at high efficiency and high yield, the amount of the hypochlorite is preferably 0.5 to 5.0 mol, and more preferably 1.0 to 3.0 mol, per 1 mol of the adamantane.

A preferable organic solvent used in the present invention is highly soluble in ruthenium in a highly oxidized state, highly resistant to oxidation, and inactive. When the organic solvent is low in solubility in ruthenium in a highly oxidized state, the reaction rate is decreased and thus the reaction time is extended. A solvent having a poor resistance to oxidation is not suitable because the solvent itself is decomposed or a byproduct is generated. Examples of such a preferable organic solvent include, for example, alkyl halides such as dichloromethane, 1,2-dichloroethane, chloroform, carbon tetrachloride, 1,1,2-trichloroethane, 1,4-dichlorobutane, 1,6-dichlorohexane and the like; esters such as methyl acetate, ethyl acetate, isopropyl acetate and the like; aryl halides such as hexachlorobenzene, benzotrifluoride ($\alpha,\alpha,\alpha$-trifluorotoluene) and the like; and aliphatic hydrocarbons such as hexane, heptane, octane and the like. These solvents may be used independently or in a system in which two or more thereof are mixed. The solvent is used preferably in an amount of 0.1 to 50 parts by weight, and more preferably in an amount of 1 to 30 parts by weight, per 1 part by weight of the adamantane used as the material.

An inorganic adsorbent used in the present invention may be any inorganic adsorbent, with no specific limitation, which has an adsorbability or an ion exchangeability and is not oxidized by a ruthenium compound and thus can coexist with the ruthenium compound in a reaction system. A preferable inorganic adsorbent is at least one selected from the group consisting of a calcium phosphate, a talcite, and an amorphous aluminum silicate.

Examples of the calcium phosphate include hydroxyapatite, fluoroapatite, chloroapatite, carbonated hydroxyapatite, carbonated fluoroapatite, calcium hydrogenphosphate, calcium dihydrogenphosphate, tricalcium phosphate, and the like. Examples of the talcite include hydrotalcite. Examples of the amorphous aluminum silicate include imogolite, alloferon and the like. These substances can be used in a mixture.

Regarding the calcium phosphate, tricalcium phosphate and hydroxyapatite are especially preferable, among the substances listed above, from the viewpoint of adsorbability to a ruthenium compound and availability. Regarding the talcite, Mg—Al type hydrotalcite and Li—Al type hydrotalcite are preferable from the same viewpoint.

The amorphous aluminum silicate such as alloferon, imogolite or the like is obtained as a result of a part of a silicate being substituted with aluminum. A part of such an amorphous aluminum silicate may be substituted with another metal.

The inorganic adsorbent may be used preferably in an amount in the range of 0.1 to 100 parts by weight, and more preferably in an amount in the range of 0.5 to 20 parts by weight, per 1 part by weight of the ruthenium compound. When the amount of the inorganic adsorbent is appropriate, the ruthenium compound can be recovered easily without influencing the reaction. When the amount of the inorganic adsorbent is too small, loss of the ruthenium compound cannot be suppressed. When the amount of the inorganic adsorbent is too large, an influence of decreasing the reaction rate or causing a side reaction is exerted, which causes an economic problem. There is no specific limitation on the timing to add the inorganic adsorbent. The inorganic adsorbent may be put into the reactor in advance, or may be added immediately before the reaction is finished.

According to one embodiment of the oxidation reaction of the present invention, a reaction solvent and a material are put into a reactor, and then a ruthenium catalyst and an inorganic adsorbent are added thereto. Then, a hypochlorite as an oxidant and a pH adjusting acid are added while the temperature is raised, to start a reaction. The reaction method is preferably a batch method from the viewpoint of the operability, handling of the material, control on the reaction temperature and the like. Alternatively, a flow method may be used, by which a reaction solution containing a substrate dissolved in a reaction solvent and an aqueous solution of hypochlorite containing the catalyst and the inorganic adsorbent are adjusted in advance, and are provided to a still-type mixer (line mixer) such as, for example, a static mixer. The conditions for the oxidation reaction are as follows. The pressure is normal pressure, and the reaction temperature is in the range of 10 to 100° C., and preferably is in the range of 40 to 70° C. in order to prevent autolysis of hypochlorite. The reaction time is preferably 100 to 1500 minutes. There is no specific limitation on the reactor, and any known reactor with a stirrer is usable. It is preferable that the reactor is formed of a material which is corrosion-resistant to the ruthenium compound. For example, a reactor lined with glass or Teflon® is preferably usable.

For the oxidation reaction according to the present invention, pH value adjustment of the water phase is important, and the pH value may be optionally selected from the range of 3 to 10. It is especially preferable that the reaction is performed on the weak acid side, namely, at a pH value of 6 or lower, in order to recover ruthenium with high efficiency after the reaction is finished. In order to adjust the pH value during the reaction, an acid may be added. An acid to be added may be any of water-soluble organic acids such as formic acid, acetic acid, propionic acid and the like; and water-soluble inorganic acids such as hydrochloric acid, sulfuric acid, nitric acid, phosphoric acid and the like. From the viewpoint of purification of the reaction product, the inorganic acids are preferable. Hydrochloric acid and sulfuric acid, which have a low possibility of influencing the reaction, are more preferable. There is no specific limitation on the concentration of the acid to be used.

After the finish of the reaction, an alkali is added to the reaction mixture to increase the pH value of the reaction water phase to 7 or higher. Thus, the ruthenium compound is reduced, is precipitated as a black crystal together with the inorganic adsorbent, and is treated with solid-liquid separation by filtration or the like to be recovered. For the solid-liquid separation, a known method is usable. A method may be selected from filtration, sedimentation, centrifugation and the like. The separated catalyst and inorganic adsorbent may be washed with water or a solvent. The ruthenium compound and the inorganic adsorbent thus separated can be reused in a subsequent reaction with no further treatment.

Examples of an alkali to be added to reduce the ruthenium compound include metal hydroxides such as sodium hydroxide, potassium hydroxide, lithium hydroxide, barium hydroxide and the like; metal carbonates such as sodium carbonate, potassium carbonate, lithium carbonate, sodium hydrogencarbonate, and the like; and tetraalkylammoniumhydroxides such as tetramethylammoniumhydroxide, tetraethylammoniumhydroxide, tetrapropylammoniumhydroxide, tetrabutylammoniumhydroxide and the like. Among these substances, sodium hydroxide and potassium hydroxide are preferable. There is no specific limitation on the concentration of the alkali to be added. The alkali may be added in a solid state, or an aqueous solution of alkali is prepared in advance and added continuously or intermittently. The amount of the alkali to be added is determined such that the pH value of the reaction water phase becomes 7 or higher.

The adamantane polyol in the reaction mixture after the catalyst is separated can be separated and purified by a known method such as extraction, washing, filtration, concentration, distillation, crystallization, recrystallization or the like.

EXAMPLES

Now, the present invention will be described more specifically by way of examples. The present invention is not limited to the following examples. The amount of generated adamantane polyol contained in the water phase was analyzed by a gas chromatographer provided with an FID detector. The quantization of the ruthenium compound contained in the water phase was performed by ICP emission spectrometry after the sample was dissolved in hydrochloric acid to provide a uniform solution. The recovery efficiency of ruthenium was found as follows: after the solid-liquid separation, the amount of ruthenium which flowed into the waste water was measured, and the concentration was used to find the efficiency.

Example 1

The following substances were put into a jacket-attached glass separable flask having a capacity of 2 L and provided with a magnet induction stirrer, a thermometer, a Dimroth condenser, and a pH electrode: 54 g of adamantane, 3.6 g of tricalcium phosphate as an inorganic adsorbent (for chemical use; produced by Wako Pure Chemical Industries, Ltd.; hereinafter, referred to simply as "TCP"), 2.7 g of ruthenium chloride-n hydrate (produced by N. E. Chemcat Corporation; the Ru content is 43%, i.e., about 1.2 g of Ru), 415 ml of ethyl acetate and 400 ml of water. 1200 g of 12 wt. % aqueous solution of sodium hypochlorite was dripped. At the same time, 10 wt. % sulfuric acid was dripped so that the pH value of the reaction solution would be 3.5. The time required to drip sodium hypochlorite was about 12 hours. During the dripping of sodium hypochlorite, the temperature was adjusted to be 55° C.±5° C. After the reaction was finished, 25% sodium hydroxide solution was dripped until the pH value of the reaction solution became 7. Next, the reaction solution was kept still, the organic phase mainly containing ethyl acetate was removed by distillation, and thus a water phase containing a ruthenium compound (catalyst) and an adamantane polyol was obtained. This water phase was analyzed by gas chromatography. As a result, the yield of 1,3,5-adamantane triol was 64%. Then, the resultant water phase was treated with suction filtration to separate the ruthenium catalyst together with the inorganic adsorbent, and thus 1800 g of water phase containing the adamantane polyol was obtained as a mother liquid. The concentration of ruthenium in the water phase was quantized by ICP emission spectrometry. The result was 5.0 ppm.

Example 2

The same operation as in Example 1 was performed except that tricalcium phosphate having the ruthenium catalyst adsorbed thereto, which was separated by filtration in Example 1, was used with no further treatment, instead of newly adding tricalcium phosphate and ruthenium chloride-n hydrate. Like in Example 1, the water phase was analyzed by gas chromatography. As a result, the yield of 1,3,5-adamantane triol was 66%. The concentration of ruthenium in the resultant water phase was quantized by ICP emission spectrometry. The result was 3.7 ppm. The results are shown in Table 1.

Example 3

The same operation as in Example 1 was performed except that 3.6 g of hydroxyapatite (for research use; produced by Wako Pure Chemical Industries, Ltd.; hereinafter, referred to simply as "HAP") was added instead of tricalcium phosphate used in Example 1. Like in Example 1, the water phase was analyzed by gas chromatography. As a result, the yield of 1,3,5-adamantane triol was 66%. The concentration of ruthenium in the resultant water phase was quantized by ICP emission spectrometry. The result was 2.6 ppm. The results are shown in Table 1.

Example 4

The same operation as in Example 3 was performed except that hydroxyapatite having the ruthenium catalyst adsorbed thereto, which was separated by filtration in Example 3, was used with no further treatment, instead of newly adding hydroxyapatite and ruthenium chloride-n hydrate. Like in Example 3, the water phase was analyzed by gas chromatography. As a result, the yield of 1,3,5-adamantane triol was 66%. The concentration of ruthenium in the resultant water phase was quantized by ICP emission spectrometry. The result was 4.2 ppm. The results are shown in Table 1.

Example 5

The same operation as in Example 1 was performed except that 1.8 g of hydrotalcite (produced by Wako Pure Chemical Industries, Ltd.; hereinafter, referred to simply as "HT") was added instead of tricalcium phosphate used in Example 1. Like in Example 1, the water phase was analyzed by gas chromatography. As a result, the yield of 1,3,5-adamantane triol was 66%. The concentration of ruthenium in the resultant water phase was quantized by ICP emission spectrometry. The result was 9.5 ppm.

Comparative Example 1

The same operation as in Example 1 was performed except that tricalcium phosphate, used in Example 1, was not used. Like in Example 1, the water phase was analyzed by gas chromatography. As a result, the yield of 1,3,5-adamantane triol was 64%. The concentration of ruthenium in the resultant water phase was quantized by ICP emission spectrometry. The result was 100 ppm.

TABLE 1

|  | Type of inorganic adsorbent | Ratio of addition (inorganic adsorbent amount/ Ru amount) (times by weight) | Concentration of Ru in water phase (ppm) | Yield of 1,3,5-adamantane triol (%) |
| --- | --- | --- | --- | --- |
| Example 1 | TCP | 3.0 | 5.0 | 64 |
| Example 2 | ↑ | ↑ (reused) | 3.7 | 66 |
| Example 3 | HAP | 3.0 | 2.6 | 66 |
| Example 4 | ↑ | ↑ (reused) | 4.2 | 66 |
| Example 5 | HT | 1.5 | 9.5 | 66 |
| Comparative example 1 | — | — | 100 | 64 |

INDUSTRIAL APPLICABILITY

According to the present invention, when an adamantane polyol is prepared, a ruthenium compound, which is costly, can be separated and recovered at a high recovery ratio, and thus an intermediate material for a highly functional polymer or an intermediate for an organic drug such as, for example, a pharmaceutical or agricultural drug can be produced at low cost.

The invention claimed is:

1. A process for preparing an adamantane polyol by reacting an adamantane represented by general formula (1) with a ruthenium compound and a hypochlorite in a biphasic water/organic solvent system, the process comprising the steps of:
    adding an inorganic adsorbent to a reaction system; and
    adding an alkali to a reaction mixture to separate the ruthenium compound together with the inorganic adsorbent, and reusing the separated ruthenium compound and inorganic adsorbent in a subsequent reaction

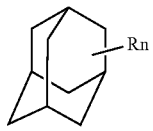

(1)

wherein the formula, a substituent Rn independently represents an alkyl group, an aryl group, a cycloalkyl group, a hydroxyl group, an alkoxy group, an aryloxy group, an acyloxy group, or a halogen group; and n is an integer of 0 to 13.

2. The process for preparing an adamantane polyol according to claim 1, wherein the inorganic adsorbent is put into a reactor in advance or added immediately before the reaction is finished.

3. The process for preparing an adamantane polyol according to claim 1, wherein the alkali is added such that a reaction water phase has a pH value of 7 or higher.

4. The process for preparing an adamantane polyol according to claim 1, wherein the inorganic adsorbent is at least one selected from the group consisting of a calcium phosphate, a talcite, and an amorphous aluminosilicate.

5. The process for preparing an adamantane polyol according to claim 4, wherein the calcium phosphate is tricalcium phosphate.

6. The process for preparing an adamantane polyol according to claim 4, wherein the talcite is hydrotalcite.

7. The process for preparing an adamantane polyol according to claim 4, wherein the calcium phosphate is hydroxyapatite.

8. The process for preparing an adamantane polyol according to claim 2, wherein the inorganic adsorbent is at least one selected from the group consisting of a calcium phosphate, a talcite, and an amorphous aluminosilicate.

9. The process for preparing an adamantane polyol according to claim 3, wherein the inorganic adsorbent is at least one selected from the group consisting of a calcium phosphate, a talcite, and an amorphous aluminosilicate.

* * * * *